United States Patent [19]

Kirkpatrick et al.

[11] Patent Number: 5,443,704
[45] Date of Patent: Aug. 22, 1995

[54] ELECTROPHORESIS GEL CONTAINER ASSEMBLIES

[75] Inventors: Francis H. Kirkpatrick, Owls Head; T. Chad Willis, Bowdinham, both of Me.; William Watt, Barto, Pa.; Henry A. Daum, III, Camden, Me.; Satyin Kaura, Oslo, Norway; Pegram A. Johnson, Wayne, Pa.

[73] Assignee: FMC Corporation, Philadelphia, Pa.

[21] Appl. No.: 816,448

[22] Filed: Dec. 31, 1991

[51] Int. Cl.6 .................... G01N 27/26; G01N 27/447
[52] U.S. Cl. ........................... 204/180.1; 204/299 R; 204/182.8
[58] Field of Search ............ 204/182.8, 299 R, 180.1, 204/301

[56] References Cited

U.S. PATENT DOCUMENTS

| | | | |
|---|---|---|---|
| 3,407,133 | 10/1968 | Oliva et al. | 204/299 R |
| 3,472,265 | 11/1969 | Elevitch | 204/182.8 |
| 3,527,712 | 9/1970 | Renn et al. | 252/312 |
| 3,715,295 | 2/1973 | Tocci | 204/180.1 |
| 3,736,100 | 5/1973 | Rains | 422/58 |
| 3,762,877 | 10/1973 | Rains et al. | 436/180 |
| 3,766,047 | 10/1973 | Elevitch | 204/299 R |
| 3,767,560 | 10/1973 | Elevitch | 204/299 R |
| 3,875,045 | 4/1975 | Bergrahm et al. | 204/182.8 X |
| 4,048,377 | 9/1977 | Boschetti et al. | 428/474.4 |
| 4,111,784 | 9/1978 | Dahms | 204/299 EC |
| 4,294,684 | 10/1981 | Serwer | 204/299 R |
| 4,314,897 | 2/1982 | Monte et al. | 204/299 R |
| 4,483,885 | 11/1984 | Chait et al. | 427/58 |
| 4,649,026 | 3/1987 | Postle et al. | 422/56 |
| 4,709,810 | 12/1987 | Mayes | 204/182.8 X |
| 4,715,943 | 12/1987 | Place et al. | 204/299 R |
| 4,741,814 | 5/1988 | Mayes et al. | 204/299 R |
| 4,756,809 | 7/1988 | Love et al. | 204/182.8 |
| 4,759,838 | 7/1988 | Mayes et al. | 204/299 R |
| 4,795,541 | 1/1989 | Hurd et al. | 204/299 R |
| 4,820,398 | 4/1989 | Yamamoto | 204/299 R |
| 4,828,670 | 5/1989 | Sarrine | 204/299 R |
| 4,844,787 | 7/1989 | Akao et al. | 204/299 R |
| 4,861,411 | 8/1989 | Tezuka | 156/344 |
| 4,889,610 | 12/1989 | Flesher et al. | 204/182.8 X |
| 4,892,639 | 1/1990 | Sarrine et al. | 204/299 R |
| 4,909,977 | 3/1990 | Hurd et al. | 264/261 |
| 4,911,816 | 3/1990 | Love et al. | 204/299 R |
| 4,929,329 | 5/1990 | Danby et al. | 204/299 R |
| 4,954,236 | 9/1990 | Kushner et al. | 204/299 B |
| 4,975,173 | 12/1990 | Transamrit et al. | 204/299 R |
| 4,999,340 | 3/1991 | Hoffman et al. | 514/23 |
| 5,045,173 | 9/1991 | Guadagno et al. | 204/182.8 X |

FOREIGN PATENT DOCUMENTS

WO8704948 8/1987 WIPO .

OTHER PUBLICATIONS

Sambrook et al. "Molecular Cloning" 2nd Edition, Cold Springs Harbor Press 1989 *No month available.

*Primary Examiner*—John Niebling
*Assistant Examiner*—John S. Starsiak, Jr.
*Attorney, Agent, or Firm*—Mark A. Greenfield; Robert L. Andersen

[57] ABSTRACT

This invention provides electrophoresis gel container assemblies comprising at least a container element, a cover element, and means for releasably sealing the cover element to the container element; methods for fabricating and for using the container assemblies; and kits comprising the container assemblies with or without precast electrophoresis gels therein in combination with at least one electrophoresis auxiliary item.

11 Claims, 8 Drawing Sheets

ELECTROPHORESIS GEL CONTAINER ASSEMBLIES

BACKGROUND OF THE INVENTION

1. Field of the Invention

This invention relates to container assemblies for packaging prefabricated electrophoresis gels or to be cast electrophoresis gels; methods for manufacturing and using the same; and kits for employing such methods comprising the container assemblies with or without precast gels therein in combination with electrophoresis auxiliary items.

2. Statement of Related Art

Gel electrophoresis has been used for clinical diagnosis and for laboratory research for over thirty years. Originally all laboratories made (cast) their own gels for such tests, but as volume grew, prefabricated gels were manufactured for sale to clinical diagnostic laboratories, which benefitted most from their increased efficiency and standardization. Non-diagnostic laboratories normally still cast their own electrophoresis gels. It is highly desirable to introduce a faster, more uniform, and more efficient method of making such gels, since this would allow the benefits of standardization in such areas as clinical research, industrial research, and forensic and quality control testing, all of which are sensitive to the speed and efficiency of their operations.

Gels for electrophoresis are intrinsically fragile, and must be protected to allow shipment. Physical protection is needed to prevent breakage or unacceptable marring on their surfaces. The packaging must also be vaporproof, to prevent drying out of the gels, which is undesirable in a standardized product. These requirements make the packaging of prepared gels very important. An additional requirement, usually unstated, is that the resulting package must be ergonomic, in that it is reasonably easy for the user to open and employ. A variety of approaches have been taken to solve these problems.

U.S. Pat. No. 3,479,265 (Elevitch) discloses a disposable cassette whose back is sealed by a gel support film, and into which is injected a gelling mixture. The injection and relief ports are later sealed. The adhesive used to seal the film to the cassette is a non-hardening sealant, to allow the film and the gel adherent to it to be stripped from the cassette for use. These devices are believed to be in current commercial use by Ciba-Corning Diagnostics, and are sold contained in sealed moisture-proof bags.

U.S. Pat. No. 3,766,047 (Elevitch) mentions the same device, and processes for making it are described in U.S. Pat. No. 3,767,560. Joining of the cassette (the "cover") to the support film (the "base") is by rubber cement or heat seal (col. 4, line 55 ff). Since the cover is at this point coated with paraffin wax (col. 4, line 13 ff), the quality of the seal is not clear. Also described is removing the plastic cover from the gel (leaving it adhered to the base), and then coating the gel with self-hardening silicone rubber as a moisture barrier.

U.S. Pat. No. 3,407,133 (Oliva and Schultz) describes a disposable electrophoresis chamber, optionally including one or more disposable lids containing a precast gel for use in the chamber. There is no discussion of the problem of sealing or preserving the prepared gel in the lid.

U.S Pat. No. 3,715,295 (Tocci) describes a variant of the U.S. Pat. No. 3,407,133 (Oliva and Schultz) device. The major improvement appears to be a semi-solid buffer. Sealing of the entire prepared device (including gel and semi-solid buffer) may be accomplished by closure in a wrapper of metal or foil.

U.S. Pat. No. 4,649,026 (Postle, et al.) describes a method of making prepared gels in which the necessity for vapor-proof packaging is avoided by dehydration of the gel. A similar approach was taken by Renn, et al. (U.S. Pat. No. 3,527,712), Boschetti, et al. (U.S. Pat. No. 4,048,377), Hoffman and Jump (U.S. Pat. No. 4,999,340), Dahms (U.S. Pat. No. 4,111,784), and others. Rehydratable gels are simpler to handle than wet (hydrated) gels, but may still require vaporproof packaging to prevent untimely rehydration. Rehydratable gels are less convenient to use than the "ready to use" gels, which are the primary focus of the present invention.

U.S. Pat. No. 4,709,810 (Mayes) discloses a box for protection of thin gels precast on support film. A film of water or other liquid is used to retain the gel on the bottom of the box. The box itself does not provide a good moisture barrier, and would have to be enclosed in foil, or sealed on the opposing edges as in Elevitch (U.S. Pat. No. 3,479,265). U.S. Pat. No. 4,741,814 (Mayes, et al.) had previously described a box with a groove in the bottom for retaining the gel. Again, the moisture-barrier properties of the assembly are not described. U.S. Pat. No. 4,759,838 (Mayes et al.) also describes a box with a flange and rim which can be sealed to be airtight. No specific means of making the junction actually impervious to water vapor is described.

U.S. Pat. No. 4,314,897 (Monte and Johnson) describes a protective box for a gel (which had been cast on a backing film) in which the edge of the film is clamped between the box and the lid to restrain and protect the gel. This device may be sealed by placing a wax strip between the halves of the box, or by enclosing the entire box in a foil or other vaporproof bag. In commercial use, the gels of this system (believed to be sold as the Beckman Paragon TM system) are sealed in foil bags.

U.S. Pat. No. 4,756,809 and U.S. Pat. No. 4,911,816 (Love, et al.) describe a chamber in which a gel, which was cast outside the chamber, can be subjected to several operations, including electrophoresis and transfer to a membrane, without further disturbing the gel. These patents do not explain how to preserve gels for extended periods. They are typical of a large number of special casting cells and chambers for electrophoresis, which are not intended to be disposable and generally do not consider the problem of packaging of the gel for storage [for example, see U.S. Pat. No. 3,736,100, Rains; U.S. Pat. No. 3,762,877, Rains and Wheeler; U.S. Pat. No. 4,795,541 and 4,909,977 Hurd and Kouri; U.S. Pat. No. 4,929,329, Danby, et al.; U.S. Pat. No. 4,954,236, Vesterberg; U.S. Pat. No. 4,954,236, Kushner and Delony; U.S. Pat. No. 4,889,610, Flesher, et al.; U.S. Pat. No. 4,294,684, Serwer; U.S. Pat. No. 4,715,943, Place and Bregnard.)

U.S. Pat. No. 4,828,670 (Sarrine) and U.S. Pat. No. 4,483,885 (Chait, et al.) discuss disposable devices with printed electrodes. Packaging is not discussed. U.S. Pat. No. 4,892,639 (Sarrine, et al.) and U.S. Pat. No. 4,975,173 (Tansamrit and Guandagno), and PCT application WO 87/04948 (Stalberg) discuss plates, potentially disposable, which have buffer gel blocks. Packaging is not disclosed.

U.S. Pat. No. 4,820,398 (Yamamoto) and U.S. Pat. No. 4,861,411 (Tezuka) describe gels which are continuously cast between plastic sheets. These require additional sealing means to preserve them, such as the vaporproof bags described by U.S. Pat. No. 4,844,787 (Akao and Kato).

Consideration of the prior art as a whole shows that two general approaches are common to the problem of packaging of gels. In the first approach, exemplified by U.S. Pat. Nos. 3,479,265, 4,820,398 and 4,861,411, the gel is fabricated or packaged with its upper face adjacent to a smooth surface, and then the whole assembly (gel plus surface protector) is sealed in vaporproof foil. The second approach is epitomized by U.S. Pat. Nos. 4,314,897 and 4,709,810. In this approach, the gel, on a support film, is restrained by a plastic box so that nothing can touch its surface. The assembly is then packed in a vaporproof bag.

A more generic level of description of all of these packaging systems is that they contain three elements: A support film, to which the gel is adhered; a protective element (either a film or a box); and a superimposed vapor barrier element, typically a foil bag, which entirely surrounds the gel, its support film, and the protective element. A common design property of all of these systems is that by positively securing the gel or its support film, they prevent any motion of the gel with respect to the protective layer.

Several of the systems disclosed in the above patents have opposable flat surfaces, either between the support film and the protective element, or between portions of the protective element, which could in principle be sealed so as to form a vaporproof barrier. In practice, this is not seen in commercial products. Experimentation with sealing substances reveals a possible underlying technical reason for this situation: sealants sufficiently vaporproof to be protective also tend to be impossible to open without recourse to knife or scissors, which can damage the gel during opening of the package, especially in the designs described in U.S. Pat. No. 3,479,265 and 4,314,897. In fact, even the foil packages of the above commercial devices often require such assistance to open them.

Further, the known prior art systems are inefficient because they have several elements, and also because they require considerable manual handling during fabrication and packaging and are difficult to adapt to automatic packaging.

SUMMARY OF THE INVENTION

This invention comprises an electrophoresis gel container assembly having at least a container element, a cover element, and means for releasably sealing the cover to the container after an electrophoresis gel is cast in the container. The invention also comprises methods for using the gel without its removal from the container by placing the container within an electrophoresis chamber or by converting the chamber itself into an electrophoresis chamber by the addition of electrodes; methods for electrophoresis using the gel by removing it and placing it in a conventional electrophoresis chamber; and kits comprising the container assembly with or without a precast gel therein, in combination with one or more auxiliary electrophoresis components.

Generally, the container assembly is characterized by the elements:

[a] a container adapted to receive an electrophoresis gel, comprising a generally planar bottom and a surrounding side wall projecting upwardly from the bottom to a top; optionally and preferably with a flange distally projecting from the top of the side wall, into a plane parallel with or at an angle to the plane of the bottom;

[b] a cover adapted to contact the top of the wall or the flange around its entire periphery; and

[c] means for releasably sealing the cover to the flange.

DETAILED DESCRIPTION OF THE INVENTION

Figure 1A:
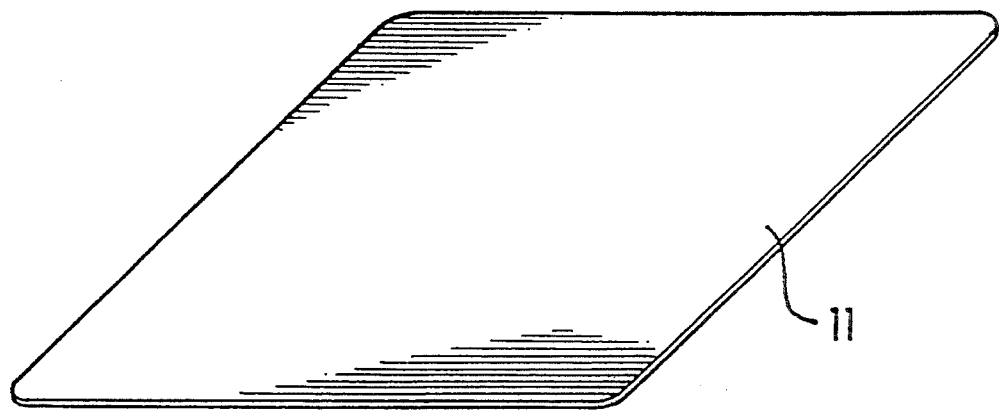
FIG. 1 is an exploded perspective view of (a) a rectangular container, (b) a gel cast within the container, and (c) a cover, according to this invention.

Other than in the operating examples, or where otherwise indicated, all numbers expressing quantities of ingredients, parameters, dimensions or reaction conditions are to be understood as modified in all instances by the term "about".

The container assemblies of this invention are characterized by comprising three primary elements.

The first element is a three-dimensional container whose bottom preferentially lies substantially in one plane, with at least one contiguous surrounding side wall rising to top which preferably has a flange projecting distally into a plane which preferably is parallel to the plane of the bottom. The bottom, the side wall, and the flange (where present) preferably are integral with each other. In top perspective, the container generally can define any regular or irregular two-dimensional shape, such as a trapezoid, rectangle, square, oval or circle, a rectangle being preferred. It also is preferable to avoid sharp joints and corners to facilitate the removal of an electrophoresis gel from the container, when desired. The flange must have a finite width to allow sealing of the cover element to the container element. This width will vary with the materials used, but will be typically at least 1 millimeter.

The second element is a cover which is at least adequate to seal the container when sealably applied to the container wall top or flange, and which preferably is shaped complementary to the top or flange. The cover is preferably planar, but may also have an indentation in the area inside the flange to decrease the headspace in the container, or to minimize movement of the gel within the container.

The third element is a means for releasably sealing the cover to the container. This means can vary. A preferred means consists of coating at least one side of the cover with a layer of meltable plastic, and heat-sealing the cover to the container under pressure. Other means are suitable, and include using a thermoformable material for the container element, the cover element, or both, and thermopressing the container and cover elements to each other; applying an adhesive to either element at appropriate points; and laminating a two sided adhesive tape between the container element and the cover element. Regardless of the means utilized, it is a critical aspect of this invention that the cover element is releasably sealed to the container element, so that it is capable of being peeled or otherwise removed therefrom to permit easy access to the container.

In a further embodiment, this invention comprises the above container assembly suitably filled with an electrophoresis-effective amount of an electrophoresis gel and with the cover releasably sealed to the container.

In other embodiments, the container shape may be modified in various ways, and/or auxiliary electrophoresis container assembly elements and/or apparatus may be provided so as to comprise a kit.

It is a preferred embodiment of this invention that the container assembly comprises materials which are sufficiently vaporproof to permit a gel sealed within the container assembly to be stored for extended periods.

The container assembly of this invention performs several functions: [a] it protects the electrophoresis gel from mechanical damage during storing and shipping;

[b] it is a mold to form the gel into a shape suitable for conducting electrophoresis in situ or for removal of the gel and placement in an electrophoresis chamber; and

[c] it comprises a vapor barrier sufficient to prevent dehydration of the gel during storage.

To fulfill its protective function, the container must comprise a material which is of adequate mechanical strength to maintain its structural integrity during filling, sealing, shipping and handling, but which also can readily be formed into a desired shape, and which in addition is a sufficient vapor barrier. A preferred material for these purposes is a plastic, especially sheet plastic, which is sufficiently malleable or moldable to be formed into the desired shape. Suitable plastic polymers include polyvinylchloride, polystyrene, polyethylene, polypropylene, polycarbonate, polyvinylalcohol, polyacrylates, polyvinylacetate, polyvinylidene difluoride, and polytetrafluoroethylene, of which polyvinylchloride and polystyrene are preferred. Such plastics are sufficiently malleable or moldable to be formed into various desired shapes. Plastic-impregnated paper, metals, glass, synthetic rubber and the like could also be used, but are not preferred.

The vapor barrier function may be afforded in several ways. The simplest and preferred, is to chose a material which has intrinsic vapor barrier qualities when used in a thickness suitable for affording the required mechanical strength. Alternatively, a vapor barrier coating may be applied to the interior or exterior surfaces of the container. It is preferred that the materials of the container assembly are selected to provide a low water vapor permeability. In particular, it is preferred that the vapor permeabiltiy is such that less than 10% of a volume of water sealed in the container assembly will permeate thought it during storage for one year at temperature in the ranges of 4° C. to 30° C. While the flange may be separately formed and fixedly adhered to the container, but it is preferred to form the flange as an integral part of the container. The materials suitable for employment as the container are generally known in the art, and this invention is not limited to a particular choice of container or cover material.

The cover can comprise any material which satisfies the requirements of sufficient vaporproofness; sealability to the container by heat or pressure or both, or other facile means of producing a vaporproof seal; and peelability or releasability, allowing the opening of the package and use of the gel without undue effort by the user. One preferred form of cover is aluminum foil coated with a releasable heat seal coating, optionally with a paper layer on the other side of the aluminum to allow printing of information on the cover. A high-tack tape, or glue, could also provide a suitable seal; however, care would be exercised in choosing a material which would both provide a vapor barrier and yet be readily releasable.

The shaping method for the container and cover will depend on the material from which they are fabricated, and could include vacuum forming, thermoforming, injection molding, cold stamping and the like. Vacuum thermoforming is especially suitable for mass production of these relatively simple shapes. The method of shaping does not form a part of this invention.

Optional additions to the system do not address the packaging, but provide features which may enhance the utility to users. One optional feature is the provision of wells in a precast electrophoresis gel for insertion of samples. Wells in electrophoresis gels are made by inserting a "comb" into the gel-forming mixture before it solidifies. The container element may have one or more pairs of slots in the side or sides to hold a comb or combs in the correct positions during gel casting, when the gel is formed directly in the container. In addition, it is possible to make the comb of inexpensive materials, so that it can be left in position after casting the gel, and sealed into the assembly with the gel. Slots are not required, however, because alternatively wells can be formed by a removable device that is supported or positioned externally to the container; or can be formed in a gel before its disposition, as a finished gel, into a container for sealing; and because some types of gels for electrophoresis do not require wells.

Figure 1B:
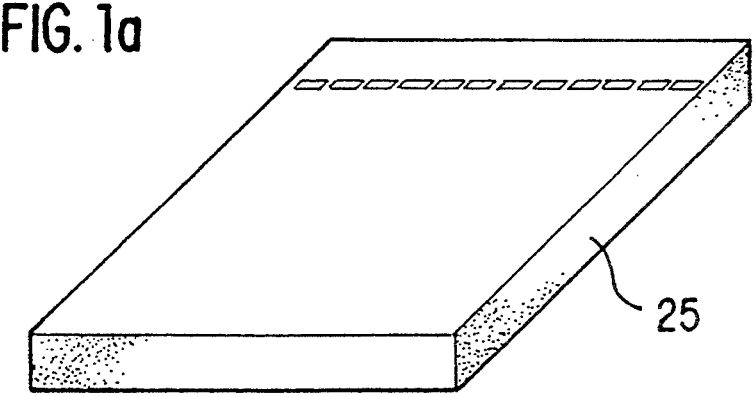
Figure 1C:
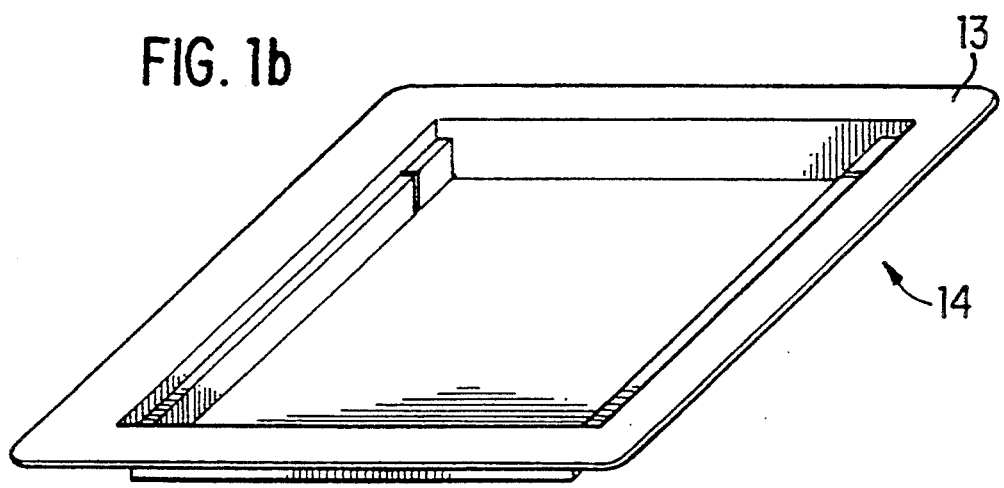
Figure 2:
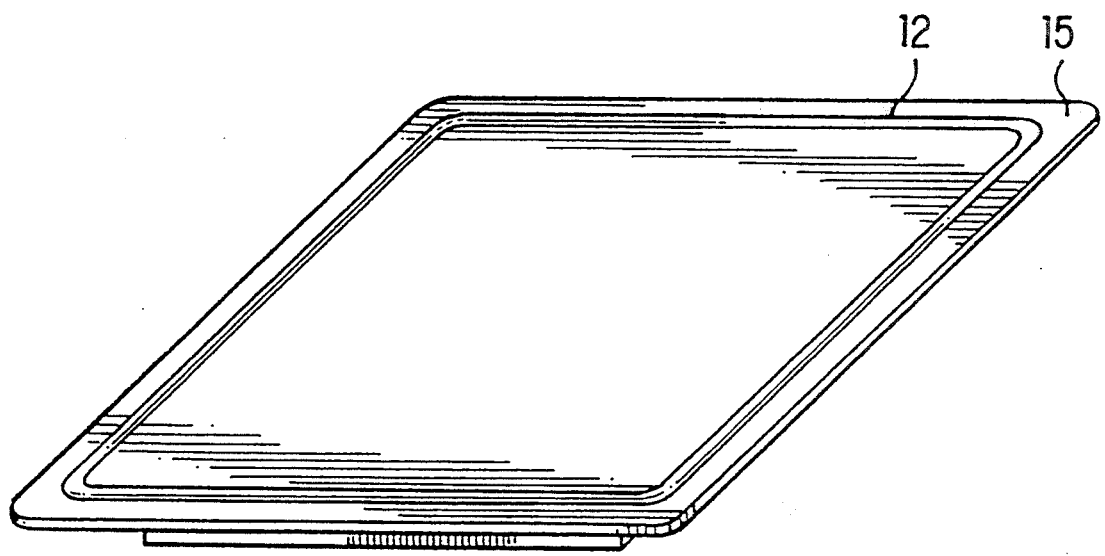
FIG. 2 is a perspective view of a rectangular container and applied cover, according to this invention.
Figure 3:
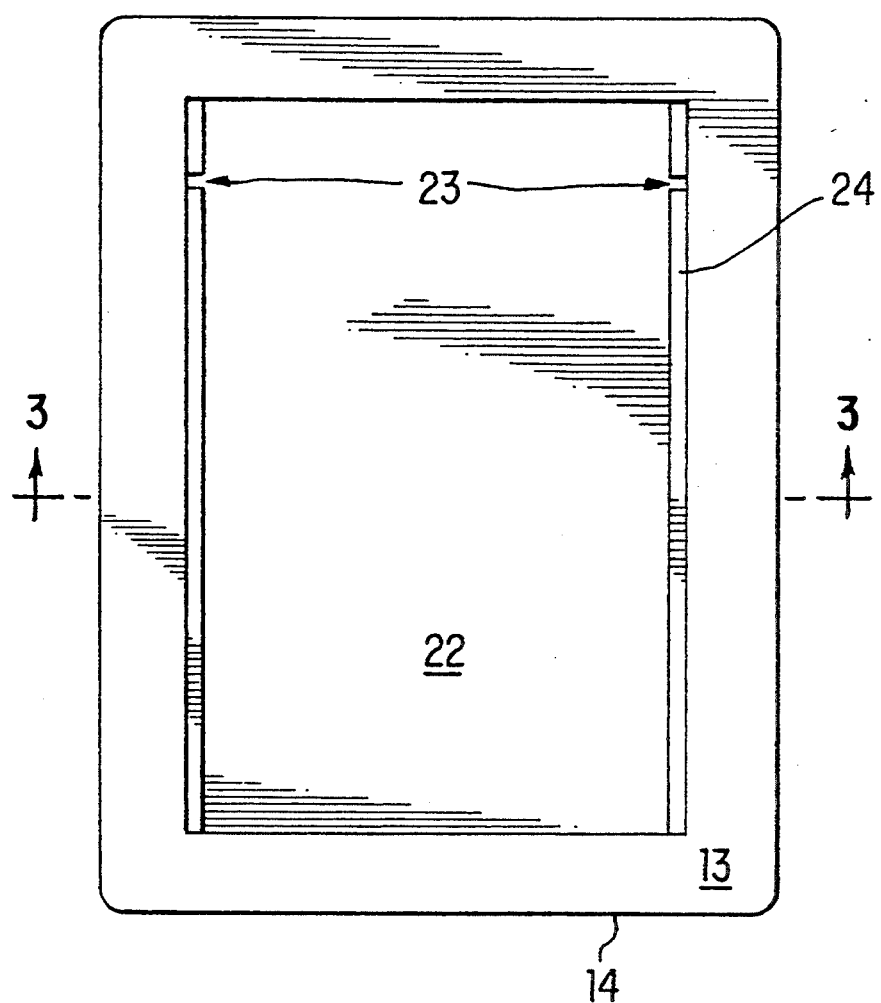
FIG. 3 is a top planar view of a container according to this invention, in which means for holding an electrophoretic gel comb are provided.

FIGS. 1, 2 and 3 illustrate a preferred embodiment of the inventive container assembly. FIG. 1 is a perspective view of a cover element 11 (FIG. 1a), a gel 25 (1b), and a container element 14 having a flange 13 (1c). The cover element 11 may have printing, such as product identification or directions for use.

FIG. 2 shows a sealed container assembly. A bead 12 resulting from heat-sealing seals the cover element to the flange of the container, thereby protecting the gel from mechanical damage and moisture loss. The cover beyond the bead (15) is not sealed, providing a strip for the user to grasp to peel the cover from the container. Although not illustrated, the flange could be narrow, so that the seal would cover the entire flange; in this case, a strip or tab of cover material extending beyond the flange would serve the same purpose.

FIG. 3 is a top view of the container 14, showing the flange 13, the bottom 22, optional slots 23, and an optional shoulder 24 for stiffening.

Figure 4:
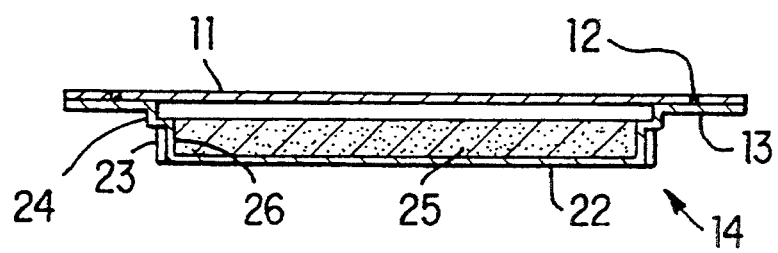
FIG. 4 is a cross-sectional view of a container assembly according to this invention.

FIG. 4 is a cross-section of FIG. 2, taken as shown in FIG. 3, and shows in addition the side walls 26.

Figure 5:
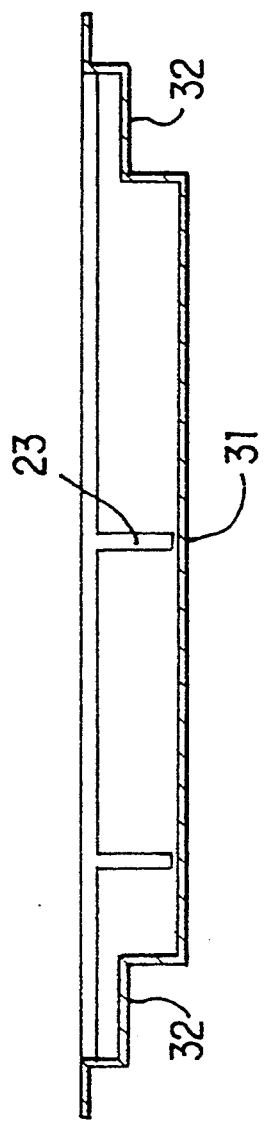
FIG. 5 is a side cross-sectional view of a container according to this invention with a depressed central section of the bottom, which is especially suited for conducting electrophoresis procedures within the container.
Figure 6:
FIG. 6 is an end cross-sectional view of FIG. 5.

FIGS. 5 and 6 show an optional feature, in which the bottom of the container is divided into three sections of differing elevation. The center section 31 is for the casting of the gel. The two outer sections 32 are intended to be flooded with buffer during electrophoresis. Two comb slots 23 are shown. (FIG. 6 is a cross-section of FIG. 5 at a comb slot.)

Figure 7:
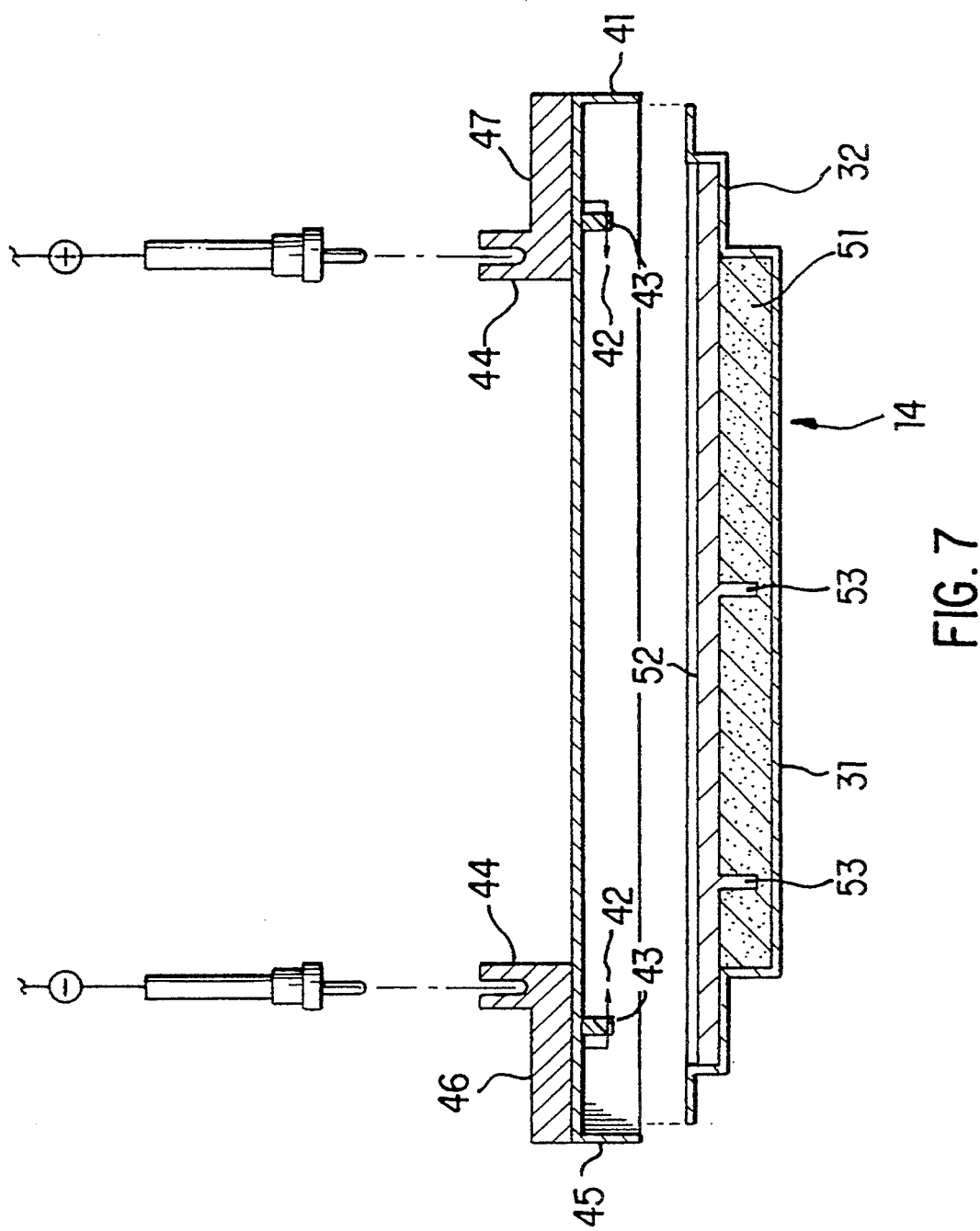
FIG. 7 is an exploded cross-sectional view of a container according to this invention with its cover removed, in conjunction with apparatus for conducting electrophoresis within the contained itself.

FIG. 7 shows the use of the container of FIG. 5. Electrodes, illustrated by an electrode carrier assembly 41 in FIG. 7, are inserted into the buffer above the outer sections 32 and the gel electrophoresis is performed directly in the container. The electrode carrier assembly 41 has electrodes 42, preferably of platinum, mounted on plastic electrode carriers 43. As illustrated, at least one electrode is connected to a jack 44 via a safety means 46. The carrier may have locating pins 45 to properly center it on the container. Alternatively, the now-vacant comb slot or slots could serve the locating function. The safety means will shut off the power to the electrodes if the carrier is removed from the container without disconnecting the power at the source. Suitable means include attitude-sensitive switches with lockouts, or conductivity detectors with lockouts. The other electrode is connected via a jack 44 to a safety means 47, or alternately via the first safety means 46. FIG. 7 also shows a gel 51 in the center section 31 of the container 14, and a layer of buffer 52 to provide electrical contact between the electrodes and the gel. Samples are deposited in wells 53 in the gel, which is illustrated as having two pairs of slots to allow deposition of two sets of samples.

Figure 8:
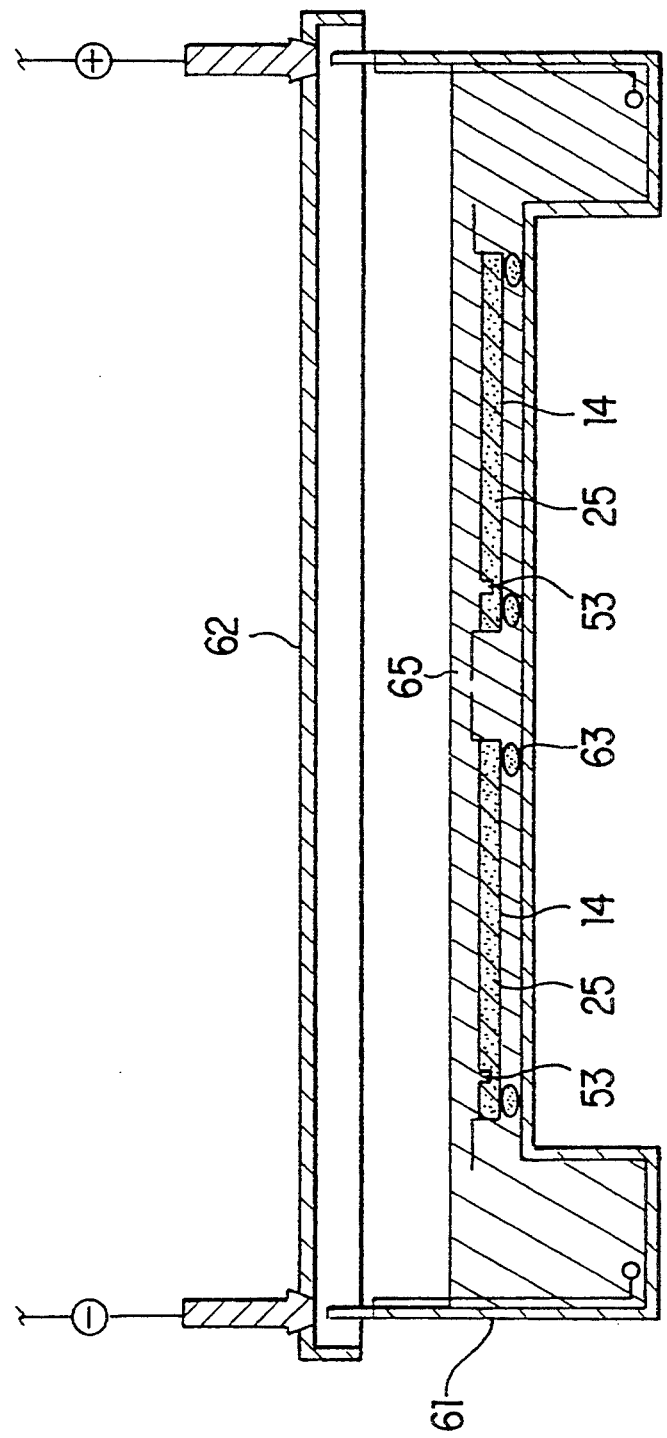
FIG. 8 is a cross-sectional view of a conventional submarine electrophoresis chamber with buffer, in which have been placed two container assemblies according to this invention (with their covers removed).

Gels can also be run, while still in their containers, in a conventional electrophoresis cell. As shown in FIG. 8, containers are opened, and set into a conventional submarine gel chamber 61. They may be held in position by adhesive strips 63, or by other means (not illustrated.) Buffer 65 is added to sufficient depth to cover the flange(s) of the container(s). Samples are loaded into the wells 53; the interlocked cover and electrical connector 62 is placed in position; and electrophoresis is conducted.

Figure 9:
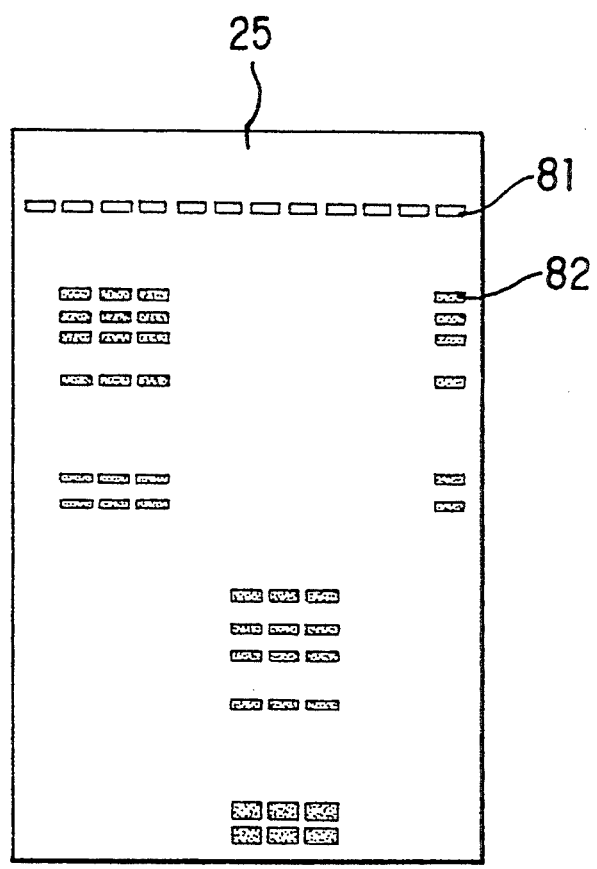
FIG. 9 is a diagram of the results obtained by electrophoresis.

FIG. 9 is a schematic illustration of the result of performing an electrophoretic separation on a gel 25, which has individual wells 81 into which samples are placed. After separation by electrophoresis, the gel is stained, revealing "bands" 82 of separated molecules, where the molecules in each band differ from those in other bands in some property, such as molecular weight.

In another embodiment, the gel is not cast directly in the container but is fabricated externally, and deposited in the container, which is then sealed by the cover element. Since no comb is required, a container without slots would be preferred for this application. The externally fabricated gel may optionally be cast on a support film. This form of gel is required by some users for the particular types of electrophoresis performed by them. It is possible to package more than one gel (especially when backed by a support film) in the same container by stacking the preformed gels in the container before sealing the cover element.

A container will be generally flat, as shown in FIG. 2 or 4, and will have a continuous side wall. The top(s) of the side wall(s) will lie in the same plane. This plane will normally be the same as that of the bottom of the container, but may also have a slant with respect to the bottom when wedge-shaped gels are to be made. The overall shape of the container will vary according to the type of electrophoresis to be performed with the gel. In most cases the container will be generally rectangular. However, a round container might be required for rotating gel electrophoresis, while a trapezoidal gel might be useful for introducing a gradient effect into the gel.

Gels suitable for use in the container assemblies do not in themselves comprise a part of this invention, but only when combined with such assemblies. Any gel may be used which is effective for electrophoresis. Such gels are preferably hydrocolloids, and include: agar, agarose, curdlan, konjac, and carrageenans including beta-carrageenan, as well as their derivatives, coprocessed mixtures and alloys; agaroses being preferred. Gels which set irreversibly or chemically may also be employed, such as crosslinked polyacrylamide, and other chemically crosslinked hydrophilic polymers, such as polyvinyl alcohol and dextran. Anaerobiosis may be required for the setting of some of these gels. Typically, the gel is employed in combination with one or more of the buffers commonly used in electrophoresis, such as TBE.

A variety of agents may be present in such gels, including: buffers; preservatives such as sodium azide; humectants; ampholytes; viscosity modifiers such as locust bean gum, dyes and stains; and the like. In any of these gel systems, it is optional to add to the gel, once formed or placed in the inventive container element, additional liquid containing the buffer used in the gel and other additives in the solution to maintain the state of the gel; followed by sealing of the inventive cover element to the container.

Devices to assist in the handling of the gel during and after electrophoresis may advantageously be included in the interior of the sealed container assembly. These include gel support films; films protecting the surface of the gel; and plastic tabs running under the gel, or other lifting means, to assist in the removal of the gel from the container.

In a further embodiment, this invention comprises a kit of the inventive container assembly, preferably containing a precast electrophoresis gel, combined with one or more auxiliary electrophoresis components. The auxiliary components are one or more: aqueous buffer solutions or buffer concentrates; staining or destaining solutions or concentrates; molecular weight standards or other standard samples; electrical devices for performing the electrophoresis, such as electrode carriers or electrodes; adhesive tape or other electrophoresis-inert adhesive of appropriate tack to affix the container in a conventional electrophoresis chamber; wicks or other conductive means for connecting the gel to a buffer solution or directly to electrodes; a carrier device with porous ends for holding the gel in place in a conventional chamber; wedges for positioning vertically-wedged gels during electrophoresis; and electrophoresis combs.

EXAMPLE 1

A container assembly according to this invention was prepared. A thermoformed container of the type shown in FIG. 3 was manufactured from sheet polyvinyl chloride of 0.5 mm (0.02 inch) thickness by thermoforming. The container was fitted with a comb and filled to a depth of 4 mm with molten SeaKem ® LE agarose (a product of FMC Corporation) dissolved at a concentration of about 1% in TBE buffer (Tris, 89 mM; boric acid, 89 mM; ethylenediaminetetraacetic acid, 2 mM; pH about 8.0). After cooling to set the agarose gel, the comb was removed. Then the container was heat sealed with a cover. The cover, available from Alcoa Corp. as "47# MG/CN, 0.001 1145/F94", was a laminate of heavy paper (to allow printing), aluminum foil (vapor barrier), and a heat-sealable release coating. It was sealed with a flat platen at 90° C. and at a pressure of 10.2 megaPascals (70 psi) for 1.3 seconds. This produced essentially the configuration of FIGS. 1–3, except for sealing the entire surface rather than just a bead.

EXAMPLE 2

A container assembly was prepared as in example 1 except that the comb was not removed before sealing.

EXAMPLE 3

Container assemblies of Example 1 and 2 were stressed to test their mechanical properties. They were repeatedly thrown to the floor, or against walls, in positions calculated to damage the gel, which was not restrained. These actions were unable to dislodge the gel sufficiently to damage it. Container assemblies were shipped by United Parcel Service from Rockland, Me. to Philadelphia and back. Most of the gels remained intact, when packaged with interleaved cardboard sheets to prevent pressure from being exerted on the comb (when present). It was discovered from these experiments that preferred containers have no comb slots and minimum clearance between the gel and the cover; and that preferred gels have a breakforce of about 1000 grams per square centimeter. Especially suitable agaroses were found to be 1% SeaKem ® LE, 1% SeaKem Gold, and 3% NuSieve ® 3:1, all available from FMC.

EXAMPLE 4

A container assembly prepared as in Example 1 was opened by peeling the cover from the container. It was possible to remove the cover manually, without requiring a knife, scissor, or other instrument. The gel was removed from the container, placed in a DNA electrophoresis minichamber, and the chamber was flooded to a depth of 2 mm above the surface of the gel with TBE buffer. DNA samples were prepared and deposited in the wells, and electrophoresis was conducted in the usual manner (see Sambrook et al., *Molecular Cloning*, 2nd Ed., Cold Spring Harbor Press, 1989). The DNA separate in a normal fashion, as expected, essentially according to the schematic of FIG. 9.

EXAMPLE 5

A container assembly prepared as in Example 1 was opened. Without removing the gel from the container, the entire assembly was placed in a gel electrophoresis chamber, which was flooded to a depth of about 2 mm above the top of the container with TBE buffer, essentially as shown in FIG. 7. DNA was applied and electrophoretically separated. The pattern of separation was normal, although it required about 20% longer to obtain the separation, possibly due to the electrical resistance of the end walls of the container.

EXAMPLE 6

A container assembly as in Example 1 was opened and the container was filled with TBE buffer to a depth of about 2 mm above the gel. DNA samples were inserted in the wells. An electrode carrier like that of FIG. 6 (but without safety interlocks) was set on the container, so that the wires ran across the container at the "front" and "back" ends, parallel to the line of wells. Voltage was applied. The DNA separated in the usual manner, taking about the same amount of time as in Example 4. In multiple tests, it was found that some tests gave wavy bands, which is undesirable (although not unknown even for standard gels and running conditions.)

EXAMPLE 7

The container configuration of FIG. 5 was emulated by trimming a container just above the gel depth, then embedding the container in a self-setting plastic in a convenient plastic container, thereby producing an interior arrangement like FIG. 5 without requiring a vacuum mold to test the concept. A gel was cast in the depressed area (element 31 of FIG. 5); the comb was removed; the device was flooded with buffer to a depth of about 4 mm above the gel and about 3 mm above the horizontal extensions of the chamber (elements 32 in FIG. 5) and DNA was added to the wells. An electrode carrier as in Example 6 was positioned with the electrodes at the outside ends of the horizontal extensions 32, and the DNA was separated by electrophoresis. A normal separation pattern was obtained. Moreover, on multiple retests, there was much less tendency for the bands to become wavy; the system behaved more like a standard minigel.

EXAMPLE 8

A container as in Example 3 which had been shipped twice across the country was opened and run as in Example 4. The gel behaved normally on electrophoresis.

EXAMPLE 9

An agarose gel as in Example 1 was cast in a mold of 0.4 mm thickness, and backed while cooling with GelBond ® support film, (available from FMC Corporation). The gel was trimmed to 6.8 by 9.8 cm (width by length) and placed in a 7 by 10 cm container. No comb was used. Buffer was added (1 ml, prepared as in example 1), and the container was sealed and commercially shipped as in Example 3. On return, the surface of the gel was unmarred, and after removal from the container and insertion in a standard serum protein electrophoresis chamber, it performed identically with a freshly-prepared gel of the same composition in the electrophoresis of serum proteins.

EXAMPLE 10

Double sided tape was obtained. ("Removable Poster Tape", cat #109 from 3M Corp.) As illustrated in FIG. 8, four gels as in Example 1, still in their containers, were adhered in place in a large chamber by applying a strip of tape to each end of the container, and then removing the backing from the other side and adhering the container to the floor of the chamber. The chamber was flooded with buffer, to a depth great enough to completely submerge the tubs; DNA was put in the wells, and electrophoresis was conducted. The tubs maintained their set positions during electrophoresis. After electrophoresis, the tubs could easily be removed from the chamber, without leaving tape adherent to the chamber. Staining of the gels confirmed that electrophoresis had proceeded normally.

We claim:

1. A container assembly for an electrophoresis gel, characterized in that it comprises:
   a) a container adapted to receive an electrophoresis gel, comprising
      a generally planar bottom,
      at least one continuous side wall projecting upward from said bottom to a top;
      a flange projecting distally from the top of said side wall;
   b) a cover, adapted to contact said flange around its entire periphery;
   c) means for releasably sealing said cover to said flange,
   d) and wherein more than one gel has been deposited within said container.

2. The container assembly of claim 1 wherein said more than one gel has been preformed.

3. The container assembly of claim 1 or 2 wherein the plane of said flange is generally parallel with said bottom.

4. The container assembly of claim 1 or 2 wherein said container is rectangular.

5. The container assembly of claim 1 or 2 wherein the materials of said container assembly are selected to provide a low water vapor permeability.

6. The container assembly of claim 5 wherein said permeability is such that less that 10% of a volume of water sealed in said container assembly will permeate through said container assembly during storage for one year at temperatures in the range of 4° C. to 30° C.

7. The container assembly of claim 1 or 2 wherein one or more pairs of recesses are formed in a side wall, adapted to hold one or more electrophoresis combs.

8. The container assembly of claim 1 or 2 wherein said bottom comprises a depression of an appropriate size and shape to accomodate an electrophoresis gel.

9. The container assembly of claim 1 or 2 wherein said more than one gel comprises a protective I layer on top of said gal.

10. A kit for electrophoresis, comprising a gel suitable for electrophoresis packaged in a container, said container having a flange and a cover sealed to said flange in a peelably releasable fashion; wherein said gel is formed outside of said container, and more than one said gel is deposited in said container before said cover is sealed to said container.

11. A method for packaging an electrophoresis gel comprising the steps of:
   preforming said gel outside of a container;
   depositing more than one said preformed gel in a container having a flange; and
   sealing said container with a cover releasably sealed to said flange.

* * * * *